(12) United States Patent
Kuboshima et al.

(10) Patent No.: US 7,371,578 B2
(45) Date of Patent: May 13, 2008

(54) METHOD OF EVALUATING THE CATALYTIC ACTIVITY OF A RARE EARTH ALKOXIDE

(75) Inventors: Yoshinori Kuboshima, Mizuho-machi (JP); Shigeki Matsunaga, Tokyo (JP); Masakatsu Shibasaki, Mitaka (JP)

(73) Assignee: Kabushikikaisha Kojundokagaku Kenkyusho (JP)

( * ) Notice: Subject to any disclaimer, the term of this patent is extended or adjusted under 35 U.S.C. 154(b) by 584 days.

(21) Appl. No.: 10/431,225

(22) Filed: May 7, 2003

(65) Prior Publication Data

US 2003/0228698 A1   Dec. 11, 2003

(30) Foreign Application Priority Data

Jun. 3, 2002   (JP) .............................. 2002-197936

(51) Int. Cl.
*G01N 31/10* (2006.01)
(52) U.S. Cl. ..................... 436/37; 436/161; 436/183
(58) Field of Classification Search ................ 436/37, 436/161, 183
See application file for complete search history.

(56) References Cited

U.S. PATENT DOCUMENTS 6,201,123 B1 *   3/2001   Daikai et al. ................. 546/21

FOREIGN PATENT DOCUMENTS

JP         10-120668       *  5/1998

OTHER PUBLICATIONS

Bougauchi, M. et al, Journal of the American Chemical Society 1997, 119, 2329-2330.*
Daikai, K. et al, Tetrahedron Letters 1998, 39, 7321-7322.*
Watanabe, S. et al, Tetrahedron Letters 1998, 39, 7353-7356.*
Nemoto, T. et al, Journal of the American Chemical Society 2001, 123, 2725-2732.*
Chen, R. et al, Tetrahedron Letters 2001, 42, 6919-6921.*
Nemoto, T. et al, Journal of the American Chemical Society 2001, 123, 9474-9475.*
Chen, R. et al, Tetrahedron 2001, 57, 9837-9842.*
Sekine, A. et al, Tetrahedron 2002, 58, 75-82.*
Sugihara, H. et al, Tetrahedron Letters 2002, 43, 2735-2739.*
Daikai, K. et al, Kidorui 1998, 32, 298-299.*
Inanaga, J., Kidorui 1999, 34, 190-191.*
Chen, R.-F. et al, Chinese Journal of Chemistry 2001, 19, 1225-1231.*

\* cited by examiner

*Primary Examiner*—Arlen Soderquist
(74) *Attorney, Agent, or Firm*—Fattibene and Fattibene; Paul A. Fattibene; Arthur T. Fattibene

(57) ABSTRACT

This invention provides a method of evaluating the catalytic activity of a rare earth alkoxide used as a starting material of a basic catalyst or an asymmetric synthesis catalyst. The rare earth alkoxide used as the subject of evaluation and 2,2'-dihydroxy-1, 1'-binaphthol are used as the starting material to prepare a rare earth complex catalyst which is then used to conduct the asymmetric epoxidation of an enone. The epoxy enone formed by this reaction, the unreacted enone, and the enantiomeric excess are measured, and from these results, the catalytic activity of the rare earth alkoxide is evaluated.

3 Claims, 1 Drawing Sheet

LOT A
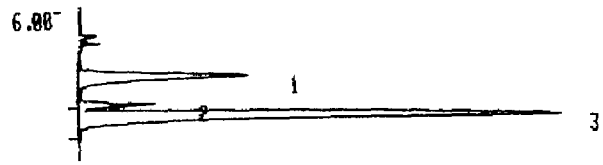
```
CAL. METHOD    00
               SF              PA              PB
        .100000₁₀+03   .100000₁₀+01   .100000₁₀+01
NO.    NAME         RT         A OR H      MK         CONC
 1                14.580      8486615                24.8823
 2                17.900      2936701       M         8.6102
 3                19.393     22693650       M        66.5073
       TOTAL                 34106966              100.0000
```
LOT B
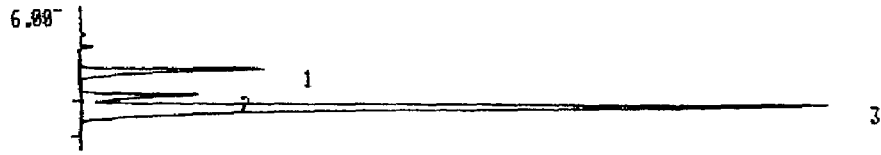
```
CAL. METHOD    00
               SF              PA              PB
        .100000₁₀+03   .100000₁₀+01   .100000₁₀+01
NO.    NAME         RT         A OR H      MK         CONC
 1                14.740      6089395                13.1217
 2                17.873      4348038       M         9.3693
 3                19.260     35969556       M        77.5089
       TOTAL                 46406990              100.0000
```
F I G. 1

METHOD OF EVALUATING THE CATALYTIC ACTIVITY OF A RARE EARTH ALKOXIDE

BACKGROUND OF THE INVENTION

1. Field of the Invention

This invention relates to a method of evaluating the catalytic activity of a rare earth alkoxide used as a starting material of a basic catalyst and an asymmetric synthesis catalyst.

2. Description of the Related Art

The rare earth alkoxide is a basic catalyst useful for organic synthesis and used in Meerwein-Ponndorf-Verley-Oppenauer reaction (T. Okano: Quarterly Chemical Review, Organic Synthesis Using Lanthanoid (in Japanese), Gakkai Shuppan Center, No. 37, p. 130, (1998), edited by the Chemical Society of Japan). Further, Shibasaki et al. found that an La-Na-BINOL catalyst obtained by reacting a rare earth alkoxide, optically active BINOL and sodium tertiary butoxide, is useful for asymmetric Michel reaction (JP-A 8-291178) Similarly, an La-K-BINOL catalyst is useful for asymmetric hydrophosphonylation reaction (JP-A 8-325281), and an La-Li-BINOL catalyst is useful for a symmetric Mannich reaction (JP-A 10-120668).

It is empirically found that the catalytic performance thereof is influenced by the process and physical properties of the rare earth alkoxide, but the cause for the influence is not elucidated (T. Okano: Quarterly Chemical Review, organic Synthesis Using Lanthanoid (in Japanese), Gakkai Shuppan Center, No. 37, p. 130, (1998), edited by the Chemical Society of Japan), and in some cases, those rare earth alkoxides produced by the same synthesis method maybe different in the catalytic activity. For researchers and manufactures participating in synthesis using rare earth alkoxides, the supply of rare earth alkoxides of stable qualities is necessary, and a method of evaluating the catalytic activity of rare earth alkoxides has been desired for satisfying the supply.

However, there was none of literatures and patents describing the method of evaluating the catalytic activity of rare earth alkoxides.

Instrumental analysis by ICP-AES and $H^1$-NMR, the present inventors analyzed those rare earth alkoxides which when used as catalyst materials, achieved a higher and lower activity respectively, but they could not found a difference in data therebetween.

Accordingly, the present inventors prepared catalysts from rare earth alkoxides as the starting material to be evaluated, and attempted at several kinds of asymmetric reactions in a scale of 100 ml or less, to determine the degree of conversion and enantiomeric excess, but asymmetric Michel reaction and asymmetric nitroaldol reaction were insensitive to the qualities of rare earth alkoxides, and the evaluation of the rare earth alkoxides by these reactions was difficult.

SUMMARY OF THE INVENTION

This invention provides a method of evaluating a catalytic activity, which is sensitive to the qualities of rare earth alkoxides.

The present inventions used rare earth alkoxides evaluated as the starting material to prepare Ln-BINOL catalysts, and used these catalysts to conduct the epoxidation of an enone thereby determining the degree of conversion and enantiomeric excess, and as a result, they found that this reaction is sensitive to the qualities of rare earth alkoxides.

The rare earth alkoxide was dissolved once in THF, then treated by heating at 40° C. for 3 hours and used as a starting material to prepare a catalyst, and this catalyst was used to conduct the epoxidation of an enone, and the amount of the unreacted material, the amount of the product and the enantiomeric excess were determined. As a result, the present inventors found that by these treatments, the amount of the product/the amount of the unreacted material in the reaction solution can be clearly distinguished among rare earth alkoxides depending on the their qualities.

That is, this invention is concerned with a method of evaluating the catalytic activity of a rare earth alkoxide, comprising the steps consisting of:

preparing a rare earth complex catalyst consisting of a reaction product obtained by reacting a rare earth alkoxide $Ln(OR)_3$ as the subject of evaluation wherein Ln represents a rare earth and R represents a $C_1$ to $C_5$ alkyl group, with optically active 2,2'-dihydroxy-1, 1'-binaphthol (BINOL) represented by formulas 1 and 2:

[Formula 1]

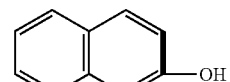

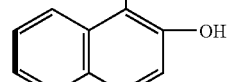

[Formula 2]

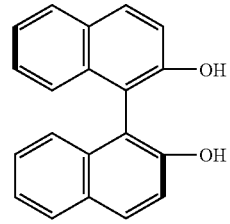

and using the reaction product to conduct the asymmetric epoxidation of an enone represented by formula 3:

[Formula 3]

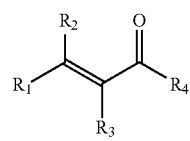

wherein $R_1$, $R_2$, $R_3$ and $R_4$ independently represent a hydrogen atom or a $C_{1-10}$ alkyl group, an aromatic group and an imidazolyl group, each of which may be substituted with a halogen atom, a $C_{1-10}$ alkyl group, an aromatic group, and an aromatic group which may be substituted with 1 to 3 halogen atoms, in order to measure the amount of an epoxy enone formed, the amount of the unreacted enone, and enantiomeric excess.

This invention is concerned with the method of evaluating the catalytic activity of a rare earth alkoxide, wherein the rare earth complex catalyst comprises a reaction product of a rare earth alkoxide, BINOL and $Ph_3P=O$.

This invention is concerned with the method of evaluating the catalytic activity of a rare earth alkoxide, wherein the enone used in asymmetric epoxidation is chalcone represented by formula 4:

[Formula 4]

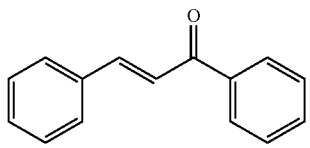

This invention is concerned with the method of evaluating the catalytic activity of a rare earth alkoxide, wherein the rare earth alkoxide dissolved in THF with water content of 20 ppm or less and then heat-treated at 35 to 60° C. is used as a starting material to prepare an asymmetric synthesis catalyst.

This invention is concerned with the method of evaluating the catalytic activity of a rare earth alkoxide, wherein the rare earth alkoxide is an La or Yb alkoxide.

This invention is concerned with the method of evaluating the catalytic activity of a rare earth alkoxide, wherein the La or Yb alkoxide is $La(O\text{-}i\text{-}C_3H_7)_3$ or $Yb(O\text{-}i\text{-}C_3H_7)_3$.

This invention is concerned with the method of evaluating the catalytic activity of a rare earth alkoxide, wherein the amounts of the epoxy enone and unreacted enone obtained in the asymmetric epoxidation are measured by high performance liquid chromatography.

BRIEF DESCRIPTION OF THE DRAWING

FIG. 1 shows HPLC results of the contents of epoxy chalcone (major, minor) and unreacted chalcone in a reaction solution after the asymmetric epoxidation of chalcone.

DETAILED DESCRIPTION OF THE INVENTION

The rare earth alkoxide used in this invention is an Sc, Y, La, Ce, Pr, Nd, Sm, Eu, Gd, Tb, Dy, Ho, Er, Tm, Yb or Lu alkoxide. In particular, the catalytic activity of La or Yb alkoxide can be well evaluated. The La alkoxide only was exemplified in the Examples in this invention, but this invention can also be applied to the Yb alkoxide. The number of carbon atoms in the alkoxyl group of the alkoxide is 1 to 5, but as the alkoxide, isopropoxide is widely used. Isopropoxide is commercially available and thus easily obtainable.

In preferable embodiments, the rare earth alkoxide is used as a solution in a solvent. The usable solvent is ether type solvent, preferably THF. Because the presence of water in the solvent inhibits accurate measurement, the solvent should be subjected to dehydration treatment to water content of 50 ppm or less. The water content is preferably 20 ppm or less.

The concentration of the solution is 0.001 to 0.5 M, preferably 0.1 to 0.3 M. The THF solution may be left at room temperature for 1 to 30 days, but for rapid evaluation, this solution is subjected preferably to heat treatment at 35 to 60° C. for 0.5 to 24 hours. This heat treatment is conducted preferably under stirring with a magnetic stirrer etc. At a treatment temperature of 35° C. or less, the number of days for treatment is increased, while at 60° C. or more, such temperature is near to the boiling point of THF, thus making heat treatment difficult in a closed system. Further, if the treatment time is too long, errors occur in analytical results.

The amount of BINOL, in terms of molar ratio to rare earth alkoxide, is 1 to 3, preferably 1. When $Ph_3P=O$ is added, the amount thereof, in terms of molar ratio to rare earth alkoxide, is 0.1 to 10, preferably 1 to 10.

The catalyst is prepared by adding the components constituting the catalyst and keeping them in a solvent in the range of −50 to 100° C. for 0.5 to 4 hours. The solvent used may be any solvent inert to the epoxylation reaction of an enone, preferably ether type solvent, particularly THF. The amount of the solvent used is 10 to 1000 ml relative to 1 mmol rare earth alkoxide.

The catalyst is prepared as a catalyst solution in a reaction system and then used in the epoxylation reaction of an enone. The reaction may be carried out by adding an oxidizing agent and an enone to the catalyst solution, or by adding an oxidizing agent to the prepared catalyst solution, then stirring the mixture, compensating for the deficiency of the oxidizing agent and adding an enone. The amount of the enone, in terms of molar ratio to rare earth alkoxide to be evaluated, is 4 to 1000.

Tertiary butyl hydroperoxide (referred to hereinafter as TBHP) used as the oxidizing agent in this invention may be used as a decane solution, or maybe extracted from 70% or 90% aqueous solution thereof with toluene, then dried over magnesium sulfate etc. and used in this invention.

As cumene hydroperoxide (referred to hereinafter as CMHP), a commercial 80 weight-% product may be used after purification or directly without purification. The amount of the oxidizing agent used, in terms of molar ratio to the enone used, is 1 or more.

In this invention, the reaction temperature is varied depending on the type of rare earth alkoxide evaluated and on the substrate for the enone, but usually the reaction is carried out is in the range of −50 to 100° C. The reaction time is 15 minutes to 24 hours.

In addition, zeolite may be used if necessary in the reaction system. The amount of zeolite used may be in any ratio to the rare earth alkoxide. Various kinds of zeolite, for example molecular sieves 3A, 4A, 5A, 13X, X and L, can be used, and in particular molecular sieve 4A is preferable.

The reaction is terminated by cooling the reaction solution to 10° C. or less or by inactivating the catalyst in the reaction system. These procedures may be combined. The inactivation of the catalyst is not particularly limited but can be carried out by adding an aqueous solution of citric acid. After the reaction is terminated, the reaction solution is extracted with an organic solvent, dried, concentrated, and purified by column chromatography to give a mixture of unreacted enone and optically active epoxy enone.

The above mixture is measured for the amount of unreacted enone (Sm), the content of epoxy enone (Pr) and the enantiomeric excess by analytical units such as HPLC. Given a rare earth alkoxide having a high catalytic activity, the value of Sm/(Pr+Sm) is low, while given a rare earth alkoxide having a low catalytic activity, this value is high. Given a rare earth alkoxide having a high catalytic activity, the enantiomeric excess is high, while given a rare earth alkoxide having a low catalytic activity, this yield is low. These values are varied significantly depending on the rare earth alkoxide evaluated and the substrate used for the enone.

Examples of the enone used in this invention include the following compounds:

Methyl vinyl ketone, trans-3-penten-2-one, trans-3-hexen-2-one,
4-methyl-1-[(2E)-1-1-oxo-3-(4-bromophenyl)-2-propenyl]-1H-imidazole, chalcone and
trans-1-phenyl-3-(4-chlorophenyl)-2-propylen-1-one.

The enone is particularly preferably chalcone represented by formula (3). Chalcone is a commercially available and easily obtainable compound. Further, chalcone and epoxy chalcone are substances easily detectable by HPLC and readily usable in this invention.

As the analytical instruments for measuring the contents of unreacted enone and epoxy enone and the enantiomeric excess, gas chromatograph, HPLC etc. can be used, but for easier measurement of enantiomeric excess, HPLC is preferably used.

Hereinafter, this invention is described in more detail by reference to the Examples.

EXAMPLE 1

Evaluation of the Catalytic Activity of Rare Earth Alkoxide by Asymmetric Epoxidation of Enone As lanthanum triisopropoxide (referred to hereinafter as La(O-i-Pr)$_3$) used as the subject of evaluation, lots A and B were used. Lots A and B were La(O-i-Pr)$_3$ produced by almost the same process, and they were almost identical in the outer appearance and color. Solutions of La(O-i-Pr)$_3$ from lots A and B in benzene-d$_6$ were analyzed respectively by $^1$H-NMR, and the data on the two were almost the same.

First, about 1 g of La(O-i-Pr)$_3$ was weighed in a globe box and then introduced into a 100-ml eggplant type flask previously heated and dried under reduced pressure, and the flask was capped with a three-way cock and taken outside. The flask was cooled well on ice, and THF was dropped slowly thereto until that the La concentration was reduced to 0.2 M, and the mixture was stirred for 5 minutes and then at room temperature for additional 5 minutes. The THF used was commercial dehydrated THF, or THF distilled from benzophenone-ketyl. When distilled THF was used, it was used after cooling to room temperature. The resulting solution was stored as a solution of La(O-i-Pr)$_3$.

(S)-BINOL (8.6 mg, 0.03 mmol), Ph$_3$As=O (9.7 mg, 0.03 mmol) and MS-4A (150 mg) were weighed in a test tube previously heated and dried under reduced pressure, and they were dried for about 10minutes under reduced pressure. THF (3.0 ml) was added thereto, then the mixture was stirred, the solution of La(O-i-Pr)$_3$ in THF (0.15 ml, 0.03 mmol) was added dropwise thereto at room temperature (22 to 23° C.), and the reaction solution was stirred at room temperature for 50 minutes, to give a solution of (S)-La-BINOL-Ph$_3$As=O complex in THF.

TBHP (0.09 ml, 0.45 mmol, 5 M decane solution) was added dropwise to the solution of (S)-La-BINOL-Ph$_3$As=O complex in THF at room temperature in an Ar gas atmosphere, and the mixture was further stirred for 10 minutes. To the yellowish white to yellow reaction solution thus obtained was added a compound (43.7 mg, 0.15 mmol) of formula 5:

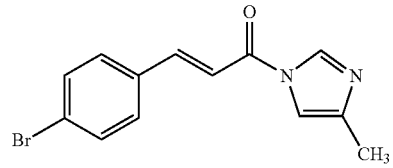

[Formula 5]

and the mixture was stirred at room temperature. After 70 minutes, methanol (0.15 ml) was added to the reaction solution, then the mixture was further stirred for 4 hours, 2% aqueous citric acid solution was added to the reaction solution, the aqueous layer was extracted with ethyl acetate, and the organic layer was washed with a brine and dried over sodium sulfate. The solvent was distilled away under reduced pressure, and the residues were purified by silica gel chromatography (ethyl acetate/hexane=1/40), to give the corresponding epoxy ester. Its enantiomeric excess was determined by HPLC (DAICEL CHIRALCEL OD; hexane/isopropanol=9/1; flow rate 0.5 ml/min.; detection at 254 nm).

The yield and enantiomeric excess in the reaction using lots A and B are as follows:

| | |
|---|---|
| Lot A Yield: 76.2% | Enantiomeric excess: 94.6% ee |
| Lot B Yield: 81.1% | Enantiomeric excess: 94.1% ee |

By conducting the asymmetric epoxidation of the enone, the catalytic activity of the alkoxide in lot A could be confirmed to be inferior to that of lot B.

COMPARATIVE EXAMPLE 1

Evaluation of the Catalytic Activity of La(O-i-Pr)$_3$ by Asymmetric Nitroaldol Reaction In this experiment too, La(O-i-Pr)$_3$ in lots A and B was used.

The method of preparing a solution of La(O-i-Pr)$_3$ was the same as in Example 1.

(S)-BINOL (17.2 mg, 0.06 mmol) was weighed in a test tube previously heated and dried under reduced pressure, and the sample in the test tube was dried for 4 hours in an oil bath at 45° C. under reduced pressure (about 2 mmHg). After drying was finished, the sample was left and cooled to room temperature and then THF (0.5 ml) was added thereto. The reaction solution was cooled on ice, and the solution of La(O-i-Pr)$_3$ (0.1 ml, 0.02 mmol) was added thereto. The ice bath was removed, and the solution was stirred at room temperature for 5 hours. Thereafter, the reaction solution was cooled again, and normal butyl lithium (44.2 μl, 0.06 mmol, 1.36M, hexane solution) was added dropwise thereto. The reaction solution was stirred at room temperature for 24 hours, and then aqueous THF (20 μl, 0.02 mmol, 1.0 M THF) was added dropwise thereto to prepare an La-Li-BINOL complex.

The La-Li-BINOL complex prepared in the method described above was used as such in nitroaldol reaction. The reaction vessel was cooled to −50° C., and nitromethane (325 μl, 6 mmol) was added slowly dropwise thereto. After the mixture was stirred at −50° C. for 1 hour, cyclohexane carboxaihyde (72.7 μl, 0.6 mmol) was added slowly dropwise thereto. After the mixture was stirred at −50° C. for 20 hours, 1.5 ml of 1 M aqueous hydrogen chloride was added to the reaction solution which was then extracted with ethyl acetate, washed with a brine and dried over magnesium sulfate. The reaction solution was concentrated, then separated by silica gel column chromatography (hexane/ethyl acetate=6/1), and its enantiomeric excess was determined by HPLC (DAICEL CHIRALPAK AD-H; hexane/isopropanol=9/1; flow rate 0.6 ml/min.; detection at 230 nm).

The yield and enantiomeric excess in the reaction using lots A and B are as follows:

| Lot A Yield: 92% | Enantiomeric excess: 91.5% ee |
| Lot B Yield: 91% | Enantiomeric excess: 92.1% ee |

The difference between lots A and B in the yield and enantiomeric excess in the asymmetric nitroaldol reaction was not higher than experimental errors, so the difference between lots A and B in the catalytic activity could not be judged.

COMPARATIVE EXAMPLE 2

Evaluation of the catalytic activity of La(O-i-Pr)$_3$ by asymmetric Michel reaction In this experiment too, La(O-i-Pr)$_3$ in lots A and B was used.

The method of preparing a solution of La(O-i-Pr)$_3$ was the same as in Example 1.

Under reduced pressure, a test tube was heated and dried with a heat gun, then provided with a three-way cock and flushed with Ar gas. An asymmetric ligand (S, S)-linked BINOL (95.88 w/w %, 16.0 mg, 0.025 mmol) was weighed in the test tube and dissolved in 0.17 ml THF (just after distilled from benzophenone ketyl) at room temperature. After cooled to −78° C., the solution of La(O-i-Pr)$_3$ (0.125 ml, 0.025 mmol) was added thereto and stirred at −78° C. for 5 minutes. Further, the reaction mixture was stirred at room temperature for 2 hours, and the solvent was distilled away under reduced pressure, and the residues were dried for 2 hours under reduced pressure, to give La-linked-BINOL complex powder.

The La-linked BINOL complex was cooled to −78° C. with dry ice-acetone in an Ar gas atmosphere and dissolved in DME (0.375 ml, just after distilled from benzophenone ketyl). Dibenzyl 2-aryl-malonate (1.0 M THF solution, 0.25 ml, 0.25 mmol) was added thereto. Further, 2-cyclopenten-1-one (21 µl, 0.25 mmol) was added thereto, and the mixture was stirred at that temperature for 5 minutes. Further, the reaction mixture was stirred at 4° C. for 83 hours, and the reaction solution was diluted with ethyl acetate and washed with an aqueous ammonium chloride solution, and the organic layer was dried over sodium sulfate.

The solvent was distilled away under reduced pressure, and the residues were purified by silica gel chromatography (ethyl acetate/hexane=1/5), whereby a Michel product was obtained as colorless oily material. The enantiomeric excess was determined by HPLC (DAICEL CHIRALCEL OJ-H, hexane/isopropanol=9/1; flow rate 0.8 ml/min.; detection at 210 nm).

The yield and enantiomeric excess in the reaction using lots A and B are as follows:

| Lot A Yield: 54% | Enantiomeric excess: 99.1% ee |
| Lot B Yield: 55% | Enantiomeric excess: 99.5% ee |

The difference between lots A and B in the yield and enantiomeric excess in the Michel reaction was not higher than experimental errors, so the difference between lots A and B in the catalytic activity could not be judged.

EXAMPLE 2

Evaluation of Rare Earth Alkoxide by Asymmetric Epoxidation of Enone (2)

In this experiment too, La(O-i-Pr)$_3$ in lots A and B was used.

The method of preparing a solution of La(O-i-Pr)$_3$ was the same as in Example 1, and this solution was used after being left at room temperature in a shaded state for 20 days.

(S)-BINOL (7.2 mg, 0.025 mmol), Ph$_3$P=O (21.1 mg, 0.075 mmol) and MS-4A (500 mg) were placed in a 30 ml test tube and then dried for about 10 minutes under reduced pressure, then THF (2.5 ml) was added thereto, the mixture was stirred for 30 minutes, and 0.125 ml of the above solution of La(O-i-Pr)$_3$ was added thereto and further stirred for 1 hour, to give an La-BINOL-Ph$_3$P=O complex.

TBHP (0.06 ml, 0.3 mmol, 5 M decane solution) was added dropwise to the solution of the La-BINOL-Ph$_3$P=O complex in THF at room temperature, and the mixture was further stirred for 20 minutes and then at 0° C. for 10 minutes. To the resulting yellow reaction solution was added the starting compound (chemical 5) (29.1 mg, 0.1 mmol), and the mixture was stirred at 0° C.

After the reaction for 30 minutes, 2% citric acid solution was added thereto, then the aqueous layer was extracted with ethyl acetate, and the organic layer was washed with a brine and dried over sodium sulfate anhydride. Methanol (3.0 ml) and sodium methoxide (10.8 mg) were added to the resulting residues, and after the mixture was reacted at room temperature for about 10 minutes, ammonium chloride was added to the reaction solution, then the aqueous layer was extracted with ethyl acetate, the organic layer was washed with a brine and dried over sodium sulfate anhydride, the solvent was distilled away, and the residues were purified by silica gel chromatography (acetone/hexane=1/10), to give a mixture of the corresponding epoxy ester and derivatives of the unreacted starting material.

The amounts of derivatives of the unreacted material and the product and the enantiomeric excess were determined by HPLC (hexane/isopropanol=9/1; flow rate 0.5 ml/min.; detection at 254 nm).

The HPLC detection values of the epoxy ester and derivatives of the unreacted material and the enantiomeric excess in the reaction using lots A and B are shown in Table 1.

TABLE 1

| Lot | HPLC detection value of epoxy ester (%) | HPLC detection value of unreacted material derivatives (%) | Enantiomeric excess % ee |
| --- | --- | --- | --- |
| Lot A | 13.6 | 86.4 | 95.0 |
| Lot B | 70.3 | 29.7 | 98.1 |

The HPLC detection value of the unreacted material derivatives in the reaction solution using lot A was 86.4%, while the HPLC detection value of the unreacted material derivatives in the reaction solution using lot B was 29.7%. From these results, it can be judged that lot B when used as the catalyst material gives higher activity than that of lot A.

COMPARATIVE EXAMPLE 3

Evaluation of Rare Earth Alkoxide by Asymmetric Epoxidation of Enone (3)

This experiment was carried out in the same manner as in Example 2 except that the La(O-i-Pr)$_3$ solution was left for 2 days.

The HPLC detection values of the epoxy ester and derivatives of the unreacted material and the enantiomeric excess in the reaction using lots A and B are shown in Table 2.

TABLE 2

| Lot | HPLC detection value of epoxy ester (%) | HPLC detection value of unreacted material derivatives (%) | Enantiomeric excess % ee |
|---|---|---|---|
| Lot A | 65.5 | 31.0 | 98.3 |
| Lot B | 61.1 | 36.0 | 98.3 |

The HPLC detection values of the unreacted material derivatives in the reaction using lots A and B were 31.0% and 36.0% respectively. In this experiment, the error in the detection values was about 10%, so the two values were considered almost the same. Under these evaluation conditions, therefore, the difference in the catalytic activity between lots A and B could not be judged.

EXAMPLE 3

Effect of Heat Treatment

In this experiment too, La(O-i-Pr)$_3$ in lots A and B was used.

The method of preparing a solution of La(O-i-Pr)$_3$ was the same as in Example 1, and this solution was subjected to deterioration treatment by stirring it at 40° C. for 1, 3, and 16 hours, respectively. Lots A and B treated under the same conditions were used as the starting material to prepare catalysts respectively, and the reactions using these catalysts were simultaneously initiated. The reactions were carried out in the following manner.

TBHP (0.06 ml, 0.3 mmol, 5 M decane solution) was added dropwise to the solution of the La-BINOL-Ph$_3$P=O complex in THF at room temperature, and the mixture was further stirred for 30 minutes. To the resulting yellow solution was added the compound (formula 5) (29.1 mg, 0.1 mmol), and the mixture was stirred at room temperature.

A part of the reaction solution was sampled at 10 minute intervals after the reaction was initiated, and the presence of the unreacted material and the product contained therein was confirmed by thin-layer chromatograph (referred to hereafter as TLC) (solvent: hexane/ethyl acetate=1/3 to 9). From the disappearance of a spot shown by the starting material, the rate of conversion was easily confirmed.

The experimental results are shown in Table 3.

TABLE 3

|  | No heat treatment | Treatment time 1 hour | Treatment time 3 hours | Treatment time 16 hours |
|---|---|---|---|---|
| Conversion rate judged from TLC | A = B | B > A | B > A | A = B |

The difference in the catalytic activity between lots A and B could be confirmed by conducting heat treatment at 40° C. for 1 to 3 hours without leaving the solution at room temperature for 20 days.

EXAMPLE 4

Evaluation of the Catalytic Activity of La(O-i-Pr)$_3$ by Asymmetric Epoxidation of Chalcone (S)-BINOL (7.2 mg, 0.025 mmol) and MS-4A (500 mg) were introduced into a 30 ml test tube and dried for about 10 minutes, and dehydrated THF (2.5 ml) manufactured by Kanto Kagaku Co., Ltd. was added thereto and stirred for 30 minutes, and the La(O-i-Pr)$_3$ solution (0.125 ml, 0.025 mmol) subjected to deterioration treatment (40° C., 3 hours) by the method in Example 3 was added thereto and stirred for additional 1 hour, to prepare an La-BINOL complex. TBHP (0.15 ml, 0.75 mmol, 5 M decane solution) was added dropwise thereto at room temperature, and the mixture was stirred for 20 minutes and then at 0° C. for 10 minutes. To the yellow solution thus obtained was added chalcone (104.0 mg, 0.5 mol), and the mixture was stirred at 0° C. to initiate the reaction.

Thirty minutes after the reaction was initiated, 2% citric acid solution was added thereto, and the aqueous layer extracted with ethyl acetate, and the organic layer was washed with a brine and dried over sodium sulfate anhydride.

The reaction solution thus obtained was purified by silica gel chromatography (acetone/hexane=1/10), to give a mixture of unreacted chalcone and epoxy chalcone.

The amounts of the unreacted starting material and the product and the enantiomeric excess were determined by HPLC (hexane/isopropanol=98/2; flow rate 1.0 ml/min.; DAICEL CHIRALCEL OD; detection at 254 nm). HPLC data are shown in FIG. 1.

The unreacted chalcone, epoxy chalcone (minor) and epoxy chalcone (major) were detected at retention times of about 14 minutes and 40 seconds, 17 minutes and 50 seconds, and 19 minutes and 20 seconds, respectively.

The HPLC detection values of unreacted chalcone and epoxy chalcone and the enantiomeric excess in the reaction using lots A and B are as shown in Table 4.

TABLE 4

| Lot | HPLC detection value of epoxy chalcone (%) | HPLC detection value of unreacted chalcone (%) | Enantiomeric excess % ee |
|---|---|---|---|
| Lot A | 75.1 | 24.9 | 95.0 |
| Lot B | 86.9 | 13.1 | 98.1 |

The HPLC detection value of the unreacted chalcone in the reaction solution using lot A was 24.9%, while the HPLC detection value of the unreacted chalcone in the reaction solution using lot B was 13.1%. From this result, it can be judged that lot B when used as the catalyst material can give a higher activity than by lot A.

As described above, the method of this invention can sensitively evaluate the catalytic activity of the rare earth alkoxide.

What is claimed is:

1. A method of evaluating the catalytic activity of a rare earth alkoxide, comprising the steps of:
    preparing a rare earth alkoxide solution by dissolving a rare earth alkoxide represented by Ln(OR)$_3$ in THF having a water content of 20 ppm or less wherein Ln represents a rare earth and R represents a $C_1$ to $C_5$ alkyl group
    heat treating the rare earth alkoxide solution for 1 to 3 hours at 35° C. to 60° C.,
    adding the heat treated rare earth alkoxide solution to optically active 2,2'-dihydroxy-1,1'-binaphthol (BINOL) represented by formulae 1 or 2:

[Formula 1]

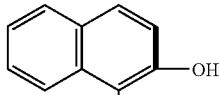

[Formula 2]

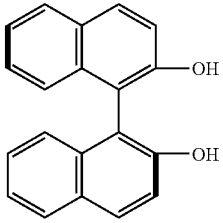

to prepare a rare earth complex catalyst, and
using the rare earth complex catalyst to conduct the asymmetric epoxidation, of an enone represented by formula 3:

[Formula 3]

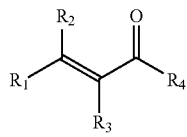

wherein $R_1$, $R_2$, $R_3$ and $R_4$ independently represent a hydrogen atom or a $C_{1-10}$ alkyl group, an aromatic group and an imidazolyl group, each of which may be substituted with a halogen atom, a $C_{1-10}$ alkyl group, an aromatic group, and an aromatic group which may be substituted with 1 to 3 halogen atoms,
whereby the amount of an epoxy enone formed in the asymmetric epoxidation, the amount of the unreacted enone, and enantiomeric excess of the epoxy enone may be measured.

2. The method of evaluating the catalytic activity of a rare earth alkoxide according to claim 1, wherein formula 3 is corresponding to chalcone in formula 1:

[Formula 4]

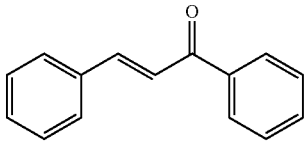

3. The method of evaluating the catalytic activity of a rare earth alkoxide according to claim 2, wherein the rare earth alkoxide represented by Ln(OR)$_3$ is La(O-i-C$_3$H$_7$)$_3$ or Yb(O-i-C$_3$H$_7$)$_3$.

* * * * *